(12) United States Patent
Krastins et al.

(10) Patent No.: US 11,877,790 B2
(45) Date of Patent: Jan. 23, 2024

(54) SURGICAL FORCEPS HAVING JAW MEMBERS

(71) Applicant: Covidien LP, Mansfield, MA (US)

(72) Inventors: Craig Krastins, Arvada, CO (US); Daniel W. Mercier, Erie, CO (US); Grant T. Sims, Boulder, CO (US)

(73) Assignee: Covidien LP, Mansfield, MA (US)

( * ) Notice: Subject to any disclaimer, the term of this patent is extended or adjusted under 35 U.S.C. 154(b) by 534 days.

(21) Appl. No.: 16/736,160

(22) Filed: Jan. 7, 2020

(65) Prior Publication Data

US 2021/0205003 A1 Jul. 8, 2021

(51) Int. Cl.
*A61B 18/14* (2006.01)
*A61B 18/00* (2006.01)

(52) U.S. Cl.
CPC ...... *A61B 18/1445* (2013.01); *A61B 2018/00589* (2013.01); *A61B 2018/00595* (2013.01); *A61B 2018/00916* (2013.01)

(58) Field of Classification Search
CPC ...... A61B 18/1445; A61B 2018/00589; A61B 2018/00595; A61B 2018/00916
See application file for complete search history.

(56) References Cited

U.S. PATENT DOCUMENTS

| 5,605,272 A | 2/1997 | Witt et al. |
|---|---|---|
| 5,891,142 A | 4/1999 | Eggers et al. |
| 5,919,206 A | 7/1999 | Gengler et al. |
| 5,935,126 A | 8/1999 | Riza |
| 6,077,287 A | 6/2000 | Taylor et al. |
| 6,129,740 A | 10/2000 | Michelson |
| 6,322,579 B1 | 11/2001 | Muller |
| 6,334,860 B1 | 1/2002 | Dorn |
| 6,443,968 B1 | 9/2002 | Holthaus et al. |
| 6,506,208 B2 | 1/2003 | Hunt et al. |
| 6,706,056 B2 | 3/2004 | Bacher |
| 6,770,072 B1 | 8/2004 | Truckai et al. |
| 6,790,217 B2 | 9/2004 | Schulze et al. |

(Continued)

FOREIGN PATENT DOCUMENTS

| AU | 2004216575 A1 | 4/2005 |
|---|---|---|
| CA | 2442598 A1 | 10/2002 |

(Continued)

*Primary Examiner* — Linda C Dvorak
*Assistant Examiner* — Ryan T Clark
(74) *Attorney, Agent, or Firm* — Carter, DeLuca & Farrell LLP

(57) ABSTRACT

An electrosurgical instrument includes a housing and an elongated shaft extending from the housing. An end effector is disposed at a distal portion of the elongated shaft. The end effector is configured to deliver electrosurgical energy to tissue. The end effector includes a first jaw member having a first electrode plate and a second jaw member having a second electrode plate. A movable handle is operably coupled to the housing. The movable handle is configured to move at least one of the first or second jaw members between an open position and a closed position. A first plate is disposed on the first jaw member. A second plate is disposed on the first plate. The second plate includes an opening defined therein. A bead is disposed on the first plate and is configured to protrude through the opening defined in the second plate.

20 Claims, 7 Drawing Sheets

(56) References Cited

U.S. PATENT DOCUMENTS

| | | |
|---|---|---|
| 6,887,240 B1 | 5/2005 | Lands et al. |
| 7,052,496 B2 | 5/2006 | Yamauchi |
| 7,147,638 B2 | 12/2006 | Chapman et al. |
| 7,150,097 B2 | 12/2006 | Sremcich et al. |
| 7,384,420 B2 | 6/2008 | Dycus et al. |
| 7,494,501 B2 | 2/2009 | Ahlberg et al. |
| 7,549,988 B2 | 6/2009 | Eberl et al. |
| 7,559,940 B2 | 7/2009 | McGuire et al. |
| 7,753,909 B2 | 7/2010 | Chapman et al. |
| 7,758,608 B2 | 7/2010 | DiCesare et al. |
| 7,766,910 B2 | 8/2010 | Hixson et al. |
| 7,877,853 B2 | 2/2011 | Unger et al. |
| 7,879,035 B2 | 2/2011 | Garrison et al. |
| 7,922,953 B2 | 4/2011 | Guerra |
| 8,241,320 B2 | 8/2012 | Lyons et al. |
| 8,252,021 B2 | 8/2012 | Boulnois et al. |
| 8,266,783 B2 | 9/2012 | Brandt et al. |
| 8,388,646 B2 | 3/2013 | Chojin |
| 8,394,094 B2 | 3/2013 | Edwards et al. |
| 8,409,244 B2 | 4/2013 | Hinman et al. |
| 8,545,534 B2 | 10/2013 | Ahlberg et al. |
| 8,551,090 B2 | 10/2013 | Sutter et al. |
| 8,728,118 B2 | 5/2014 | Hinman et al. |
| 8,740,933 B2 | 6/2014 | Anderson |
| 8,789,741 B2 | 7/2014 | Baxter, III et al. |
| 8,814,856 B2 | 8/2014 | Elmouelhi et al. |
| 8,858,553 B2 | 10/2014 | Chojin |
| 10,098,689 B2 | 10/2018 | Soni |
| 10,639,091 B2 * | 5/2020 | Jones ................ A61B 18/1445 |
| 2005/0090837 A1 | 4/2005 | Sixto et al. |
| 2006/0052778 A1 * | 3/2006 | Chapman ........... A61B 18/1442 |
| | | 606/51 |
| 2010/0063525 A1 | 3/2010 | Beaupre et al. |
| 2011/0270245 A1 | 11/2011 | Horner et al. |
| 2011/0270251 A1 | 11/2011 | Horner et al. |
| 2013/0071282 A1 | 3/2013 | Fry |
| 2014/0025073 A1 | 1/2014 | Twomey et al. |
| 2016/0074099 A1 * | 3/2016 | Kappus ............. A61B 18/1445 |
| | | 29/434 |
| 2016/0199123 A1 * | 7/2016 | Thomas ............ A61B 18/1445 |
| | | 264/250 |
| 2018/0193087 A1 | 7/2018 | Dycus et al. |
| 2021/0307859 A1 * | 10/2021 | Nelson .................. A61B 90/03 |

FOREIGN PATENT DOCUMENTS

| | | |
|---|---|---|
| CA | 2844067 A1 | 9/2014 |
| EP | 2319447 A1 | 5/2011 |

* cited by examiner

SURGICAL FORCEPS HAVING JAW MEMBERS

BACKGROUND

Technical Field

The present disclosure relates to surgical instruments and methods and, more particularly, to surgical forceps having jaw members configured to seal tissue.

Background of Related Art

Open or endoscopic electrosurgical forceps utilize both mechanical clamping action and electrical energy to effect hemostasis. The electrode of each opposing jaw member is charged to a different electric potential such that when the jaw members grasp tissue, electrical energy can be selectively transferred through the tissue. A surgeon can treat tissue by either cauterizing, coagulating/desiccating, sealing, and/or simply reducing or slowing bleeding, by controlling the intensity, frequency and duration of the electrosurgical energy applied between the electrodes and through the tissue.

In order to promote accurate, consistent and effective, sealing and other tissue treatment effects, one or more insulative stop members may be positioned along one or both opposed surfaces of the jaw members to maintain a specific gap distance between the jaw members when the jaw members are in a clamping position with tissue grasped therebetween.

The stop members may be secured to the opposed surfaces of the jaw members via one or more suitable securement methods. The current techniques of forming and securing the stop members to the opposed surfaces of the jaw members may require specialty equipment, precise tolerances, and/or introduce process variability which increases the manufacturing cost of the jaw members.

SUMMARY

An electrosurgical instrument provided in accordance with aspects of the present disclosure includes a housing and an elongated shaft extending from the housing. An end effector is disposed at a distal portion of the elongated shaft. The end effector is configured to deliver electrosurgical energy to tissue. The end effector includes a first jaw member having a first electrode plate and a second jaw member having a second electrode plate. A movable handle is operably coupled to the housing. The movable handle is configured to move at least one of the first or second jaw members between an open position and a closed position. A first plate is disposed on the first jaw member. A second plate is disposed on the first plate. The second plate includes an opening defined therein. A bead is disposed on the first plate and is configured to protrude through the opening defined in the second plate.

In aspects according to the present disclosure, the first plate includes an indent defined therein configured to support the bead.

In aspects according to the present disclosure, the first plate includes an opening defined therein that supports a bottom surface of the bead atop the first jaw member.

In aspects according to the present disclosure, the first plate and the second plate form a substantially spherical shape around the bead.

In aspects according to the present disclosure, the bead includes a lower portion having a first width and an upper portion have a second width smaller than the first width. The upper portion of the bead having the second width projects through the opening defined in the second plate.

In aspects according to the present disclosure, the end effector includes a knife configured to cut tissue disposed between the first and second jaw members.

In aspects according to the present disclosure, an activation button extends from the housing and in registration with the movable handle. Selective actuation of the movable handle controls the delivery of electrosurgical energy to the first and second jaw members.

In aspects according to the present disclosure, the bead has a substantially spherical shape.

In aspects according to the present disclosure, the first plate and the second plate are mechanically welded together.

An electrosurgical instrument provided in accordance with aspects of the present disclosure includes an electrosurgical instrument including a housing and an elongated shaft extending from the housing. An end effector is disposed at a distal portion of the elongated shaft. The end effector is configured to deliver electrosurgical energy to tissue. The end effector includes a first jaw member and a second jaw member. At least the first jaw member includes a jaw support including a plurality of capture tabs disposed thereon. A movable handle is operably coupled to the housing and is configured to move at least one of the first or second jaw members between an open position and a closed position. A series of spacers are disposed on the jaw support and are seated between the capture tabs. A sealing plate includes a corresponding series of openings defined therethrough configured to capture each respective spacer such that each spacer protrudes therethrough. An insulative housing is configured to secure the sealing plate atop the jaw support.

A method of manufacturing an electrosurgical instrument in accordance with aspects of the present disclosure includes positioning a first plate including a plurality of indents on a first jaw member of an end effector assembly. The method includes positioning at least one bead in an indent of the plurality of indents. The method includes positioning a second plate on the first plate and on the at least one bead. The second plate includes at least one opening defined therein. The at least one opening is configured to expose a surface of the bead facing away from the first plate. The method includes attaching the first plate to the second plate to capture the at least one bead between the first plate and the second plate.

In aspects according to the present disclosure, a first base plate is positioned on the first jaw member. A second base plate is positioned on the first base plate. The second base plate forms a laterally facing attachment notch with the first base plate. An overmold layer is formed about the first jaw member. The overmold layer is formed in the laterally facing attachment notch to secure the first and second base plates to the first jaw member.

In aspects according to the present disclosure, the spacer is coupled to the first jaw member.

In aspects according to the present disclosure, the first base plate includes an opening aligned with an opening of the second base plate. In other aspects according to the present disclosure, the overmold layer extends through the openings of the first and second base plates.

In aspects according to the present disclosure, a method of manufacturing an electrosurgical instrument includes: positioning a first base plate including a plurality of indents on a first jaw member of an end effector assembly; positioning one or more spacers in an indent of the plurality of indents; positioning a second base plate having one or more openings defined therein on the first base plate and on the one or more spacers, the one or more openings exposing a surface of the spacer facing away from the first base plate, the second base plate forming a laterally facing attachment notch with the first base plate; forming an overmold layer about the first jaw member in the laterally facing attachment notch to secure the first and second base plates to the first jaw member.

In aspects according to the present disclosure, a first overmold layer is formed about the first jaw member. In other aspects according to the present disclosure, the first overmold layer penetrates the first opening and the second opening to vertically secure the first and second base plates to the first jaw member. In still other aspects according to the present disclosure, the method includes forming a second overmold layer about the first overmold layer, the second overmold layer formed in the laterally facing attachment notch to laterally secure the first and second base plates to the first jaw member.

In aspects according to the present disclosure, the method includes forming the first overmold layer about the first jaw member, the first overmold layer forming a first tip protrusion at a distal portion of a first jaw member and the spacer and the first tip protrusion maintaining a substantially continuous distance between the first and second jaw members in the closed position.

In aspects according to the present disclosure, the method includes forming a second overmold layer about the second jaw member, the second overmold layer forming a second tip protrusion at a distal portion of the second jaw member, the second tip protrusion directly contacting the first tip protrusion when the first and second jaw members are in the closed position.

In aspects according to the present disclosure, the first and second base plates form an overhang extending distally from the first jaw member and the first overmold layer is formed about the overhang formed by the first and second base plates.

In aspects according to the present disclosure, the spacer and the first tip protrusion maintain a substantially continuous distance between the first and second jaw members in the closed position.

BRIEF DESCRIPTION OF THE DRAWINGS

The accompanying drawings, which are incorporated in and constitute a part of this specification, illustrate embodiments of the present disclosure and, together with the detailed description below, serve to further explain the present disclosure, in which.

DETAILED DESCRIPTION

Figure 1:
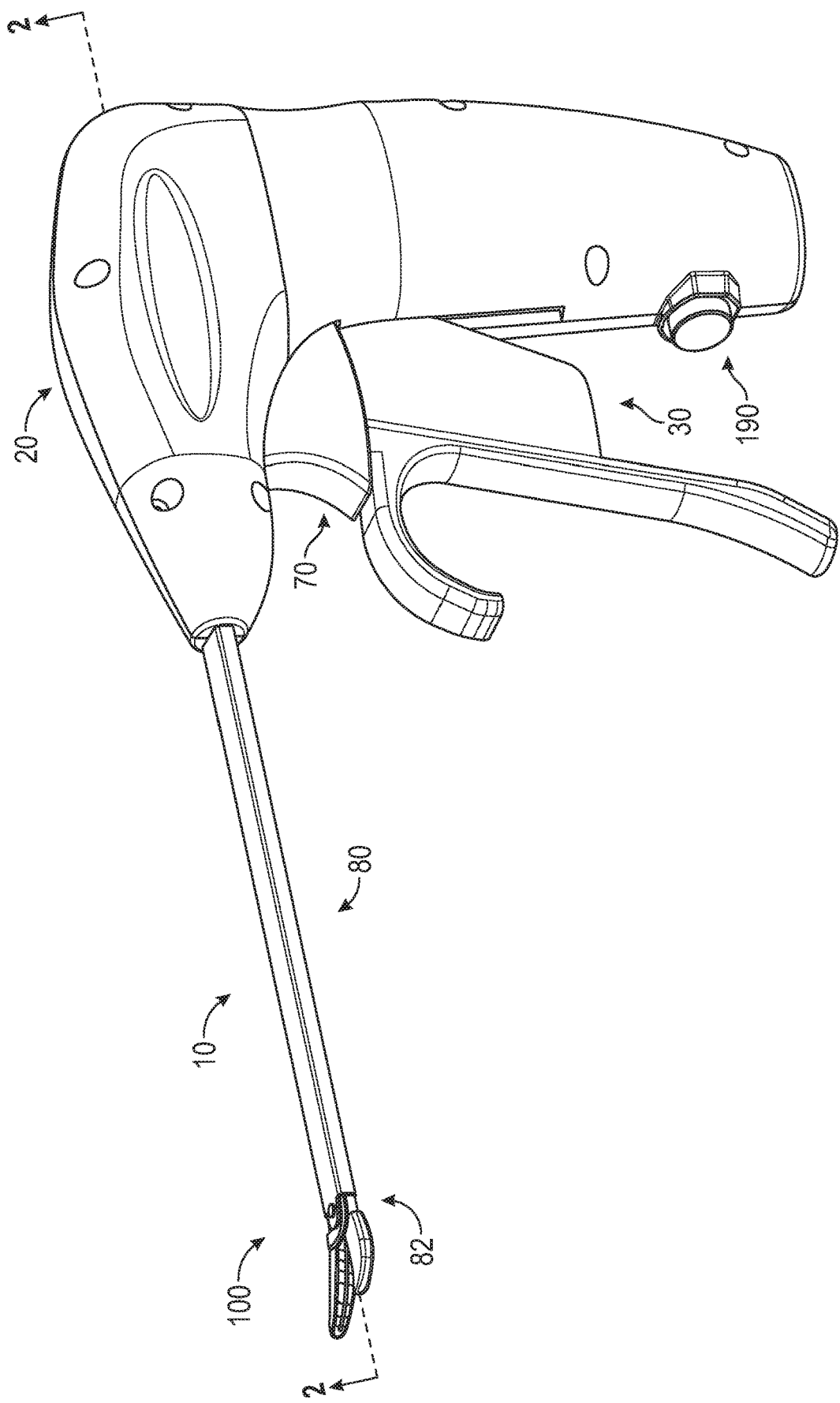
FIG. 1 is a perspective view of an electrosurgical instrument according to the present disclosure with jaw members of the end effector assembly disposed in an open position.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

"About" or "approximately" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

Descriptions of technical features or aspects of an exemplary embodiment of the present disclosure should typically be considered as available and applicable to other similar features or aspects in another exemplary embodiment of the present disclosure. Accordingly, technical features described herein according to one exemplary embodiment of the present disclosure may be applicable to other exemplary embodiments of the present disclosure, and thus duplicative descriptions may be omitted herein.

Exemplary embodiments of the present disclosure will be described more fully below (e.g., with reference to the accompanying drawings). Like reference numerals may refer to like elements throughout the specification and drawings.

Figure 2A:
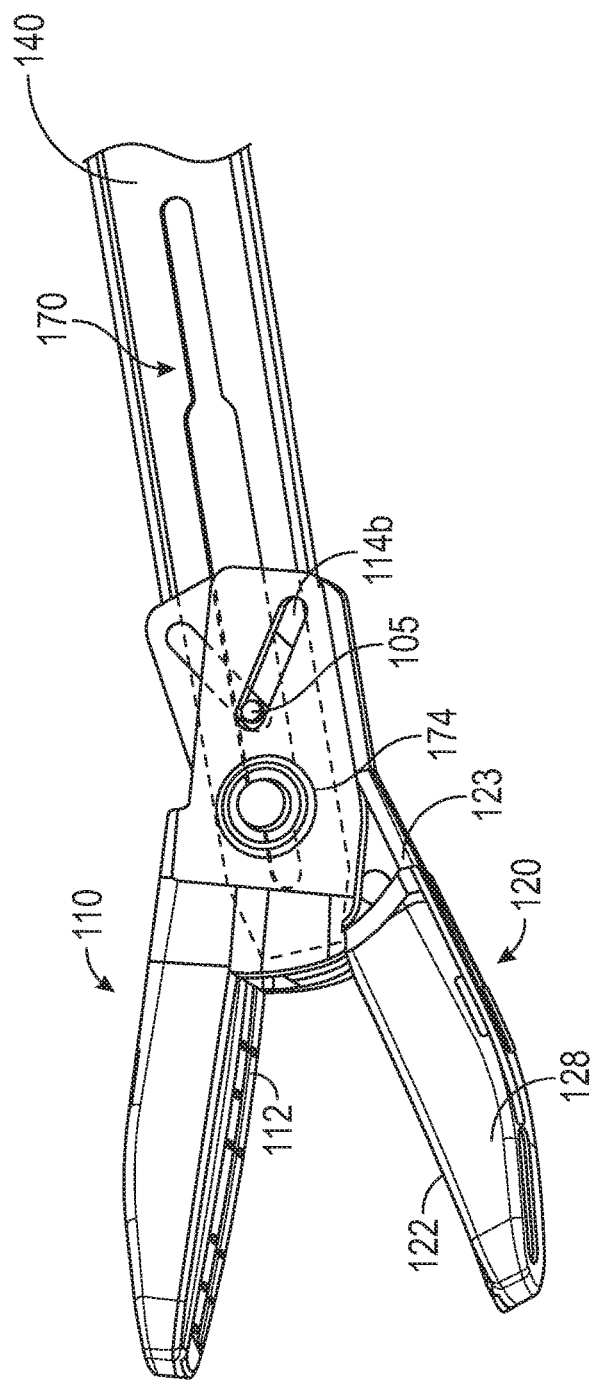
FIG. 2A is an enlarged perspective view of the electrosurgical instrument of FIG. 1 with jaw members of the end effector in an open position.
Figure 2B:
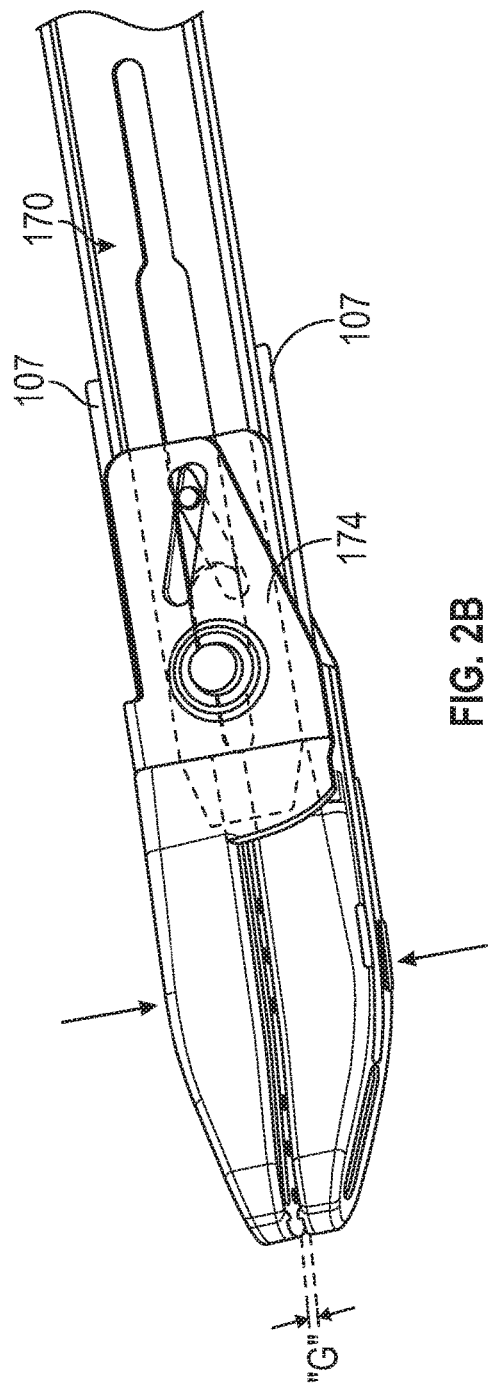
FIG. 2B is an enlarged perspective view of the electrosurgical instrument of FIG. 1 with jaw members of the end effector in a closed position.

Referring generally to FIGS. 1, 2A and 2B, a surgical instrument provided in accordance with the present disclosure is shown generally identified by reference numeral 10. Instrument 10, as described below, is configured for grasping, treating, and/or dissecting tissue and may find particular applicability for use in performing tonsillectomy and/or adenoidectomy procedures, although use of instrument 10 in various other surgical procedures is also contemplated and within the scope of the present disclosure.

Instrument 10 generally includes a housing 20, a handle assembly 30, a trigger assembly 70, a shaft 80, an end effector assembly 100, a drive assembly 140, a knife assembly 170, and an energy activation assembly 190. Shaft 80 extends distally from housing 20 (e.g., along a plane 2-2—see, e.g., FIG. 1) and supports end effector assembly 100 at distal end 82 thereof. Drive assembly 140 operably couples handle assembly 30 with end effector assembly 100 to enable selective manipulation of jaw members 110, 120 of end effector assembly 100. Knife assembly 170 is operably coupled with trigger assembly 70 to enable selective translation of a knife blade 174 of knife assembly 170 relative to end effector assembly 100. Energy activation assembly 190 enables energy to be selectively delivered to end effector assembly 100.

Instrument 10 may also include an electrosurgical cable (not shown) that connects instrument 10 to a generator (not shown) or other suitable power source, although instrument 10 may alternatively be configured as a battery-powered instrument. The electrosurgical cable includes lead wires, e.g., lead wires 107, extending therethrough that have sufficient length to extend through housing 20 and shaft 80 in order to operably couple the generator, energy activation assembly 190, and end effector assembly 100 with one another to enable the selective supply of energy to electrically-conductive plates 112, 122 of jaw members 110, 120 of end effector assembly 100, e.g., upon activation of energy activation assembly 190.

For a more detailed description of instrument 10, reference may be made to U.S. Pat. No. 9,918,779, entitled "SURGICAL INSTRUMENTS AND METHODS FOR PERFORMING TONSILLECTOMY, ADENOIDECTOMY, AND OTHER SURGICAL PROCEDURES," the entire contents of which are incorporated by reference herein. However, the aspects and features of the present disclosure are equally applicable for use with other suitable surgical instruments.

Although only the features of jaw member 110 or jaw member 120 are described below and/or illustrated in the figures, it is noted that jaw members 110, 120 defines mirror-image configurations of one another (unless specifically contradicted herein) and, thus, any description and/or illustration of one jaw member 110, 120 applies similarly to the other jaw member 110, 120.

Referring to FIGS. 1, 2A, 2B, 3A, 3B and 3C, electrosurgical instrument provided in accordance with aspects of the present disclosure includes housing 20 and elongated shaft 80 extending from the housing 20. The end effector 100 is disposed at a distal portion of the elongated shaft 80. The end effector 100 is configured to deliver electrosurgical energy to tissue. The end effector 100 includes first jaw member 110 having a first electrode plate 112 and second jaw member 120 having a second electrode plate 122.

Movable handle 30 is operably coupled to the housing 20. The movable handle 30 is configured to move at least one of the first or second jaw members 110 or 120 between an open position (see, e.g., FIG. 2A) and a closed position (see, e.g., FIG. 2B).

The end effector 100 includes the knife 170 configured to cut tissue disposed between the jaw members 110 and 120. The activation button 190 extends from the housing 20 and is in registration with the movable handle 30. Selective actuation of the movable handle 30 controls the delivery of electrosurgical energy to the jaw members 110 and 120. Actuation of the moveable handle 30 also controls opening and closing of the end effector 100.

A spacer 300 is positioned on jaw member 110 (although it is envisioned that the spacer 300 may be disposed on jaw member 120). The spacer 300 may be ball-like or cylindrical in nature and may be made from a ceramic, glass, metal or the like. As an example, the spacer 300 may be conical in shape. As explained in more detail below, the spacer 300 is configured to operably engage a first plate 301 disposed on a support base 116 of jaw member 110. First plate 301 and support base 116 may be separate components or may be integral with one another.

A second plate 302 is disposed on or atop the first plate 301 in vertical registry therewith. Second plate 302 may include one or more mechanical features (not shown) that facilitate alignment atop first plate 301 or that facilitate secure engagement with first plate 301. The second plate 302 includes one or more openings 303 defined therein. One or more beads 304 is disposed atop (or is otherwise engaged with) the first plate 301 and each bead is configured to protrude through a respective opening 303 defined in the second plate 302. The bead(s) may be made from metal, glass, ceramic, plastic, minerals, or another type of material depending upon a particular purpose. The description of the first and second plates 301 and 302 with respect to the first jaw member 110 is similarly applicable to the second jaw member 120. Thus, either or both of the first and second jaw members 110 and/or 120 may include a two plate construction technique as described herein.

In a configuration in which each of the first and second jaw members 110 and 120 include beads (e.g., beads 304) as described herein, a bead positioned on the first jaw member 110 may directly contact a corresponding bead positioned on the second jaw member 120.

The beads 304 are captured between the first plate 301 and the second plate 302, while protruding through an upper surface of the second plate 302 to oppose jaw member 120. When the end effector 100 is in a closed configuration, upper surfaces 405 of the beads 304 contact jaw member 120 to maintain a predetermined distance between jaw member 110 and jaw member 120. Further, when the end effector 100 is in a closed configuration, upper surfaces 405 of the beads 304 increase the overall grasping strength of the jaw members 110 and 120 when grasping tissue therebetween.

The first plate 301 may include indents 305 defined therein configured to support the one or more beads 304. As described in more detail below, a lower surface 404 of the bead 304 is positioned in the indent 305 of the first plate 301 during an initial manufacturing step (see, e.g., FIG. 3A).

Figure 4A:
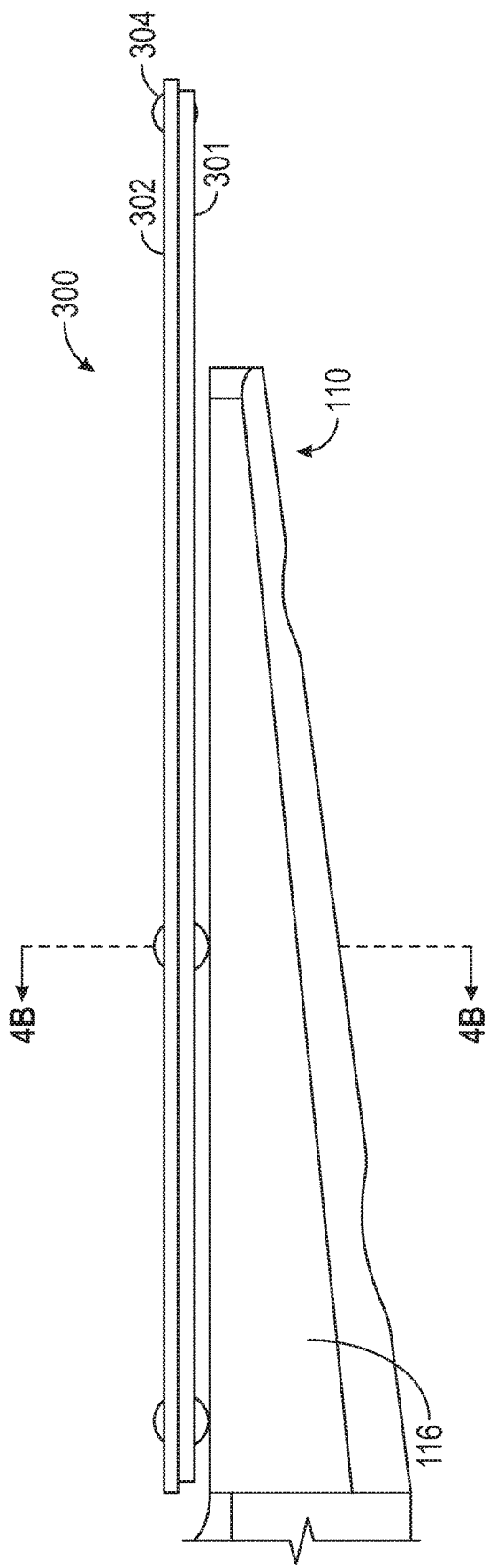
FIG. 4A is an enlarged side view of the spacer disposed through both the first plate and through the second plate.
Figure 4B:
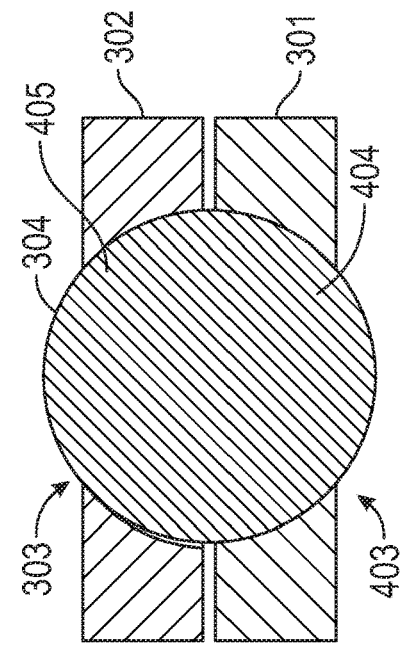
FIG. 4B is a greatly enlarged cross-sectional view of the spacer taken along lines 4B-4B of FIG. 4A.
Figure 5A:
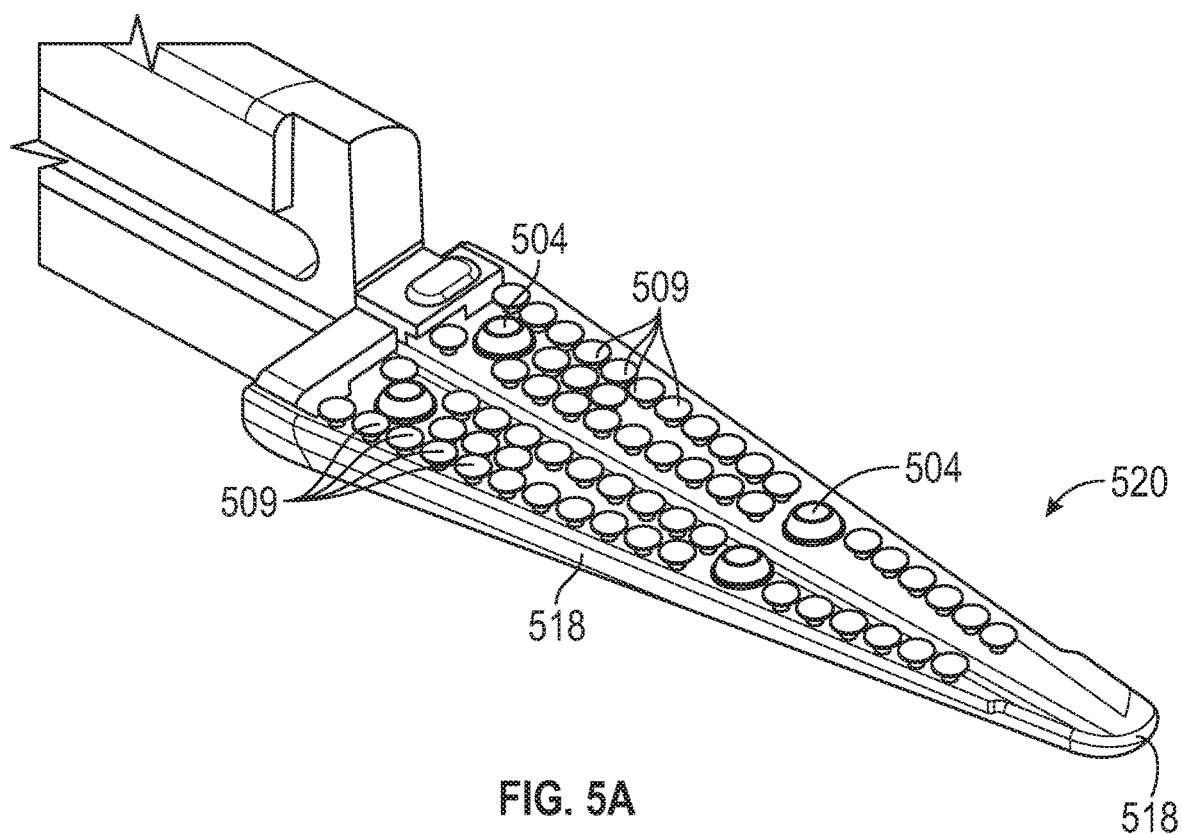
FIG. 5A is an enlarged perspective view of a plurality of spacers according to another embodiment of the present disclosure.
Figure 5B:
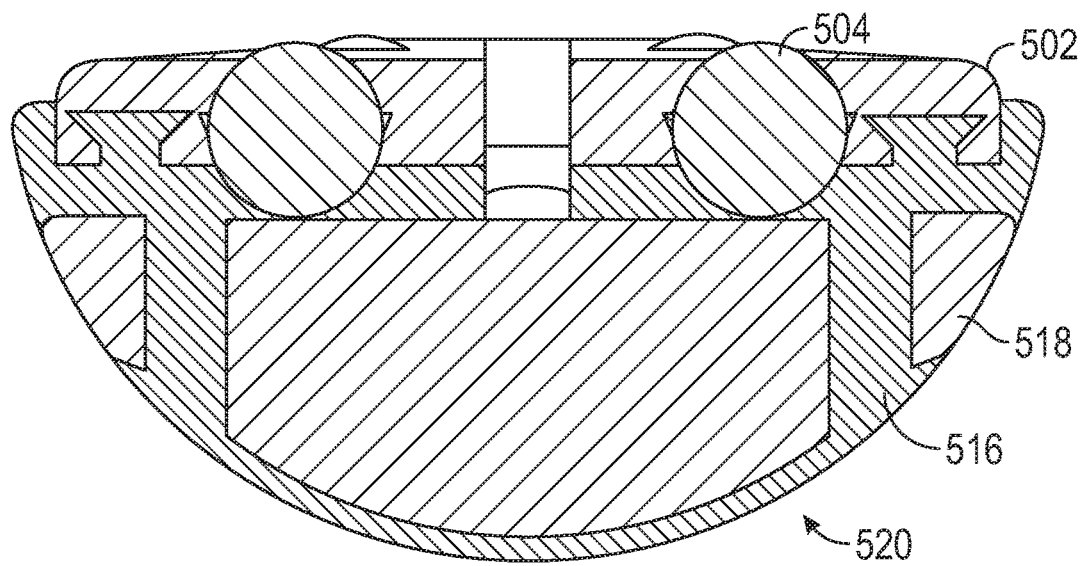
FIG. 5B is an enlarged cross-sectional view of the jaw member of FIG. 5A with a seal plate disposed thereon.

Alternatively, the first plate 301 may include one or more openings 403 defined therein (see, e.g., FIGS. 4A and 4B) that support the lower surface 404 of the beads 304 atop the jaw support of jaw member 110. Thus, when the end effector 100 is in a closed state, the lower surface 404 of the beads 304 directly contacts the support 116 of jaw member 110 and the upper surface 405 of the beads 304 directly oppose jaw member 120, thus maintaining desired spacing between jaw member 110 and jaw member 120 during sealing.

Referring back to FIGS. 3A-3C, the first plate 301 and the second plate 302 form a substantially spherical shape around the beads 304. The shape and size of the beads 304 may be substantially the same as a space formed between the first plate 301 and the second plate 302, thus capturing the beads between the first plate 301 and the second plate 302. Exemplary embodiments of the present disclosure are not limited to beads having a spherical shape, and other shapes may be employed, as desired. For example, the beads described herein may have a top-hat like shape having a relatively wide first portion and a relatively narrow second portion disposed on the first portion.

The first plate 301 and the second plate 302 may be mechanically welded together or there may be a mechanically interfacing element (not shown) between the first plate 301 in direct contact with the second plate 302 (e.g., the first and second plates 301 and 302 may be separately formed structures that are in direct contact with each other to capture the metallic glass bead 304 therebetween). The first plate 301 may be bonded with or adhered to (e.g., by welding) the second plate 302 to capture the beads 304 between the first plate 301 and the second plate 302. As an example, the first plate 301 and the second plate 302 may each be formed on beads 304. The beads 304 may include a lower portion having a first width and an upper portion have a second width smaller than the first width. The upper portion of the beads 304 may include a width that is configured to project through the opening 303 defined in the second plate 302.

The first plate 301 and the second plate 302 may be configured to stack on top of each other to allow for a force sensor and/or a temperature sensor to be positioned between the plates. The force sensor allows an amount of force generated between the jaw members 110 and 120 to be measured at either of the first or second jaw members 110 or 120. A pressure sensor may also be positioned between the first and second plates (e.g., between the first plate 301 and the second plate 302 when stacked on each other). Descriptions of jaw members 110 and/or 120 herein are similarly applicable to jaw member 520, a jaw member opposing jaw member 520 (not shown), jaw member 710 and jaw member 720 described in more detail below.

Figure 3A:
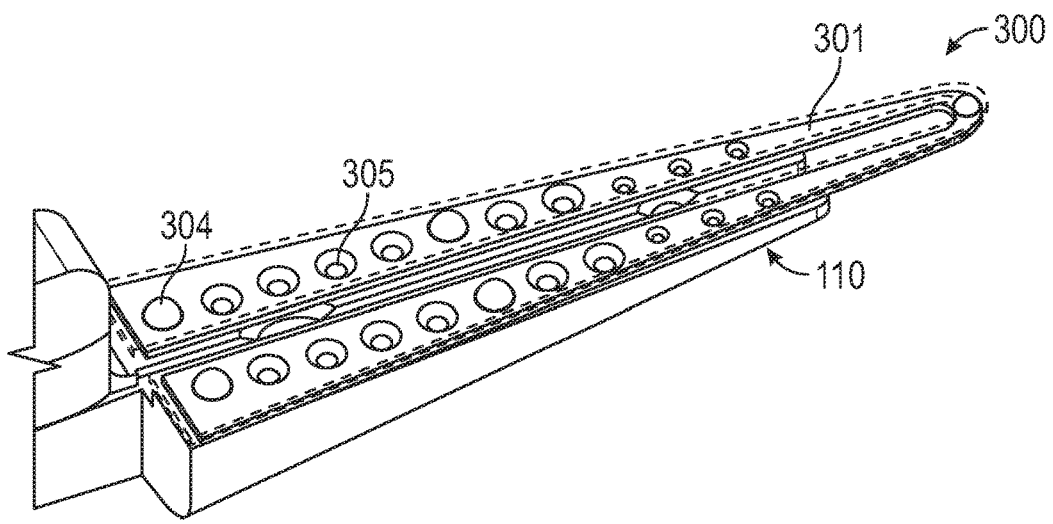
FIG. 3A is an enlarged perspective view of a spacer and one jaw member of an end effector according to the present disclosure showing a first plate disposed atop a support base of the jaw member.
Figure 3B:
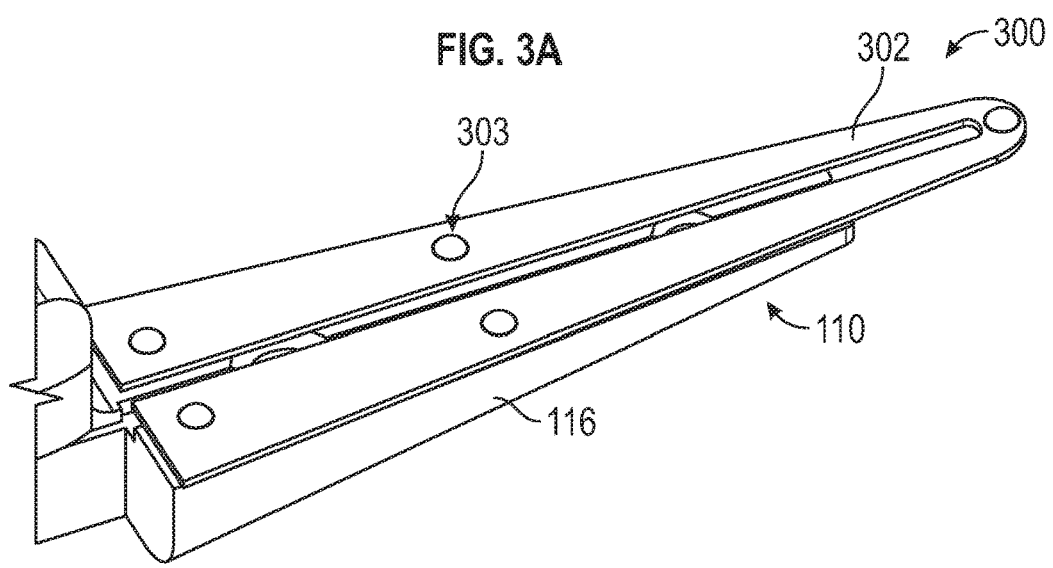
FIG. 3B is an enlarged perspective view of the jaw member of FIG. 3A with a second plate disposed atop the first plate.
Figure 3C:
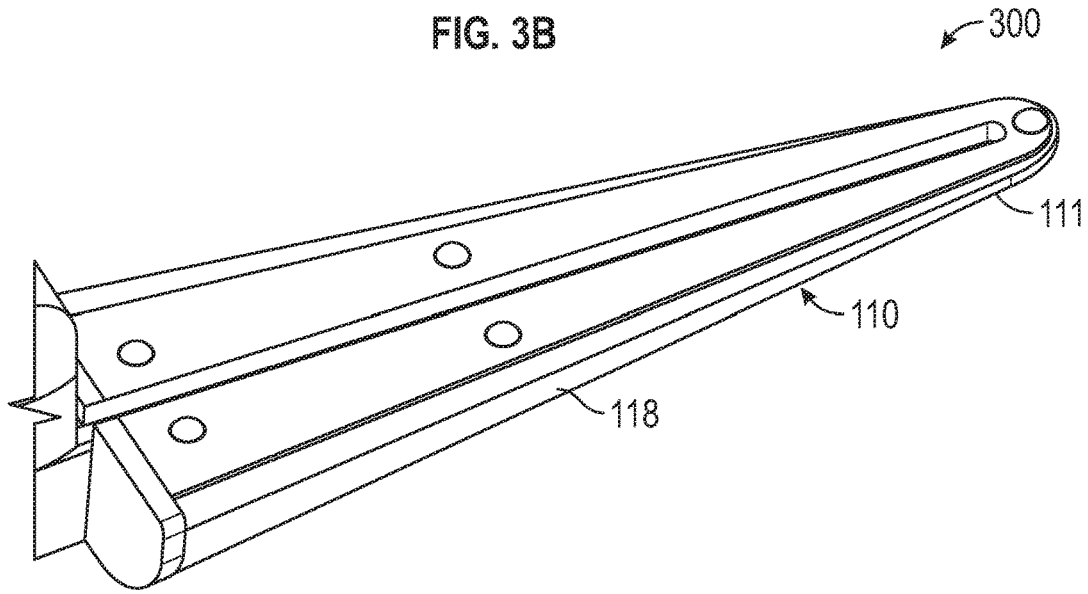
FIG. 3C is an enlarged perspective view of the jaw member of FIG. 3A with the second plate disposed atop the first plate secured by an outer insulative overmold.

The first plate 301 and the second plate 302 may be longer than the support 116 of jaw member 110 and/or jaw member 120 forming a distal overhang 111 (see, e.g., FIG. 3C) at a distal end of the support (FIGS. 3A, 3B and 3C). As a result thereof, one or more of the beads 304 may be located distally of support 116 of jaw member 110 and/or jaw member 120. However, when the first plate 301 and the second plate 302 forming a two plate construction are relatively narrow, a bead 304 is omitted distal of the support 116, as described in more detail below with reference to FIGS. 5A-7B. Further, the first plate 301 and the second plate 302 may be stacked on each other to support the distal overhang 111, thus preventing bending or warping of distal overhang 111. For example, the first plate 301 may maintain heat treated properties to increase the overall strength of spacer 300 including the first plate 301 and the second plate 302. Alternatively, one or both jaw members, e.g., jaw member 110, may include a support 116 long enough to underlie overhang 111 (e.g., support 116 is substantially the same length as the first plate 301 and the second plate 302).

Referring to FIG. 3C, insulative overmold 118 is formed around support 116 and extends to distal overhang 111. Insulative overmold 118 provides further structural support for distal overhang 111. As described in more detail below with reference to FIGS. 5A-7B, a distal portion of an overmold layer (e.g., overmolds 118, 518 or 718) positioned distal of a proximal support structure (e.g., support 116) may form a distal spacer maintaining spacing between distal portions of first and second jaw members including overhang 111.

Referring again to FIGS. 3A to 3C, a method of manufacturing an electrosurgical instrument in accordance with aspects of the present disclosure includes positioning a first plate 301 including a plurality of indents 305 on a first jaw member 110 of an end effector assembly 100. The method includes positioning at least one bead 304 in an indent of the plurality of indents 305. The method includes positioning a second plate 302 on the first plate 301 and on the at least one bead 304. The second plate 302 includes at least one opening 303 defined therein. The at least one opening 303 is configured to expose a surface of the bead 304 facing away from the first plate 301. The method includes attaching the first plate 301 to the second plate 302 to capture the at least one bead 304 between the first plate 301 and the second plate 302.

Referring to FIGS. 5A, 5B, 6A and 6B, a series of alternate spacers 504 are shown disposed along jaw member 520. An opposing jaw member (not shown) faces jaw member 520 and may have substantially the same structure and configuration as jaw member 520. More particularly, jaw member 520 includes a plurality of capture tabs 509 disposed atop the support base 516 that extend at least partially along the length thereof. Each spacer 504 is configured to seat between a series of adjacent capture tabs 509 to capture and secure each spacer 504 atop jaw support 516 (see, e.g., FIG. 5A). The capture tabs 509 may include edge tabs positioned along edges of the first or second jaw members 110 or 120. Once secured (or at least seated) atop the jaw support 516, a sealing plate 502 is secured atop the spacers 504 via an insulative housing (overmold) 518 or other mechanical securement process. Sealing plate 502 may include a series of openings (not shown) defined therein that vertically align in registry with the spacers 504 to facilitate assembly (see, e.g., FIG. 5B).

As can be appreciated, variously-sized spacers 304, 504 may be utilized along or across the jaw support 116, 516 depending upon a particular purpose. For example, spacers 304, 504 of different heights may be disposed along the jaw support 116, 516 to create different gap distances between jaw members 110, 120 when approximated. Likewise, different height spacers 304, 504 may be disposed across the jaw members 110, 120 depending on a particular purpose. Spacers 304, 504 of a first height may be disposed at the proximal and distal ends of the jaw support 116, 516 and spacers 304, 504 of a different height may be disposed therebetween. Spacers 304, 504 of different widths or diameters may also be configured along or across the jaw support 116, 516.

Figure 6A:
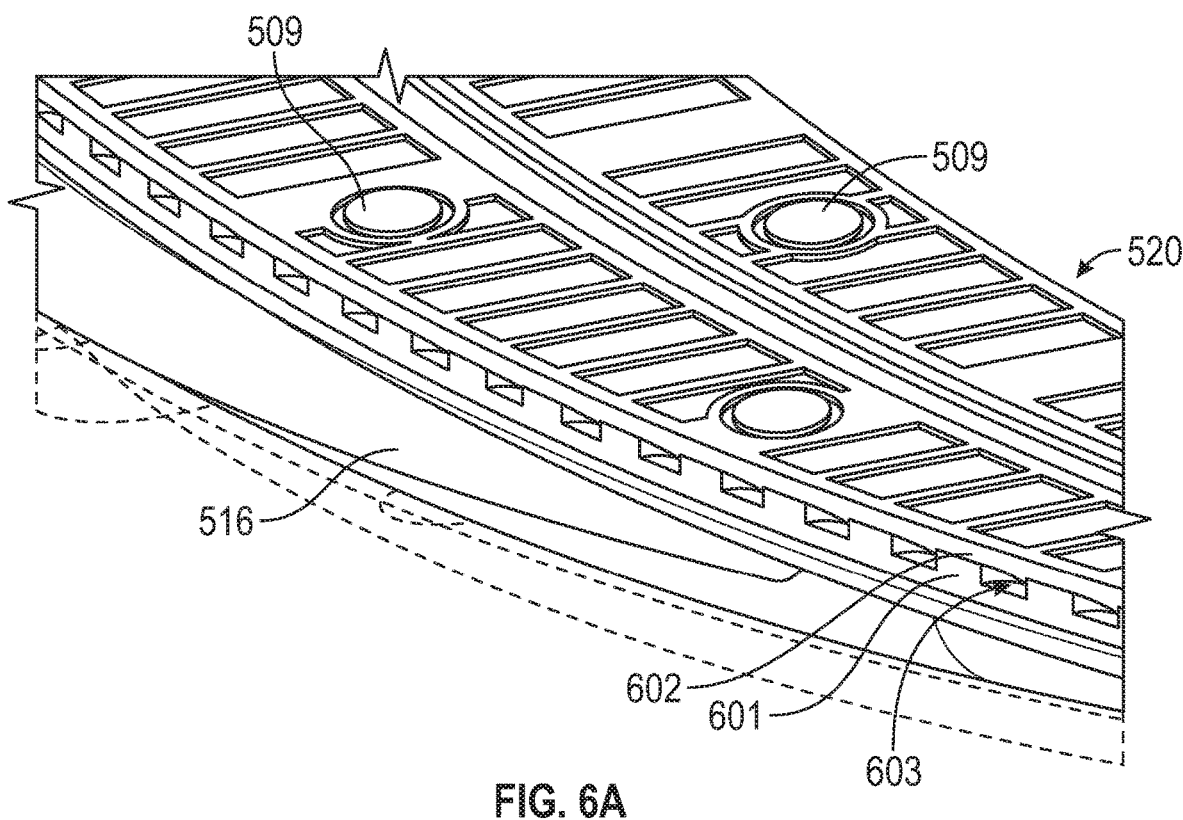
FIG. 6A is an enlarged, perspective view of a jaw member having plurality of capture tabs according to an embodiment of the present disclosure.
Figure 6B:
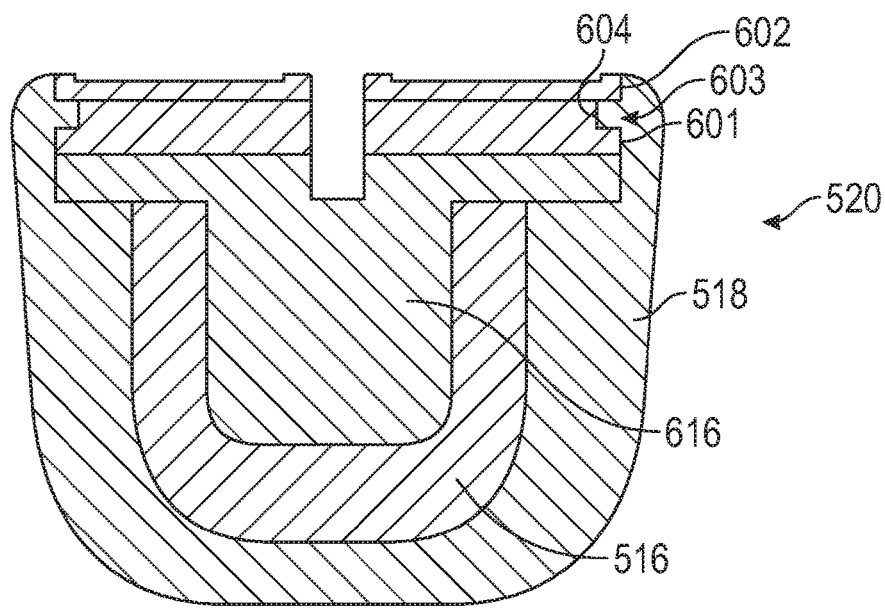
FIG. 6B is an enlarged, cross-sectional view of the jaw member of FIG. 6A illustrating a two-plate construction secured by an overmold layer.

FIG. 6A illustrates a first base plate 601 and a second base plate 602 on the first base plate 601. An attachment notch 603 formed by an inset sidewall 604 of the first base plate 601 (or alternatively, of the second base plate 602) is formed between the first and second base plates 601 and 602. In FIG. 6A, overmold layer 518 is not illustrated in order to illustrate the exposed attachment notch 603. In FIG. 6B, the overmold layer 518 is illustrated and is formed about the first attached notch 603. The technical features described with reference to the first and second plates 301 and 302 (see, e.g., FIGS. 3A to 4B) are similarly available to the first and second base plates 601 and 602 whenever technically feasible.

Referring to FIGS. 6A and 6B, the overmold layer 518 is formed about the first jaw member 520 to secure the first and second base plates 601 and 602 to the first jaw member 520. In particular, the overmold layer 518 is formed in the attachment notch 603 to secure the first and second base plates 601 and 602 to the first jaw member 520. The first and second base plates 601 and 602 may be secured to each other, for example, by mechanical welding together or any known method in the art.

The first and second base plates 601 and 602 may form a plurality of attachment notches 603 intermittently spaced apart from each other along a length of one or both lateral facing sides of the first jaw member 520. Similar attachment notches 603 may be formed on a second jaw member (not shown) facing the first jaw member 520.

A spacer (see, e.g., spacers 304 and 504) may be captured between the first and second base plates 601 and 602, as described herein. The spacer may be secured to the first jaw member 520.

Figure 6C:
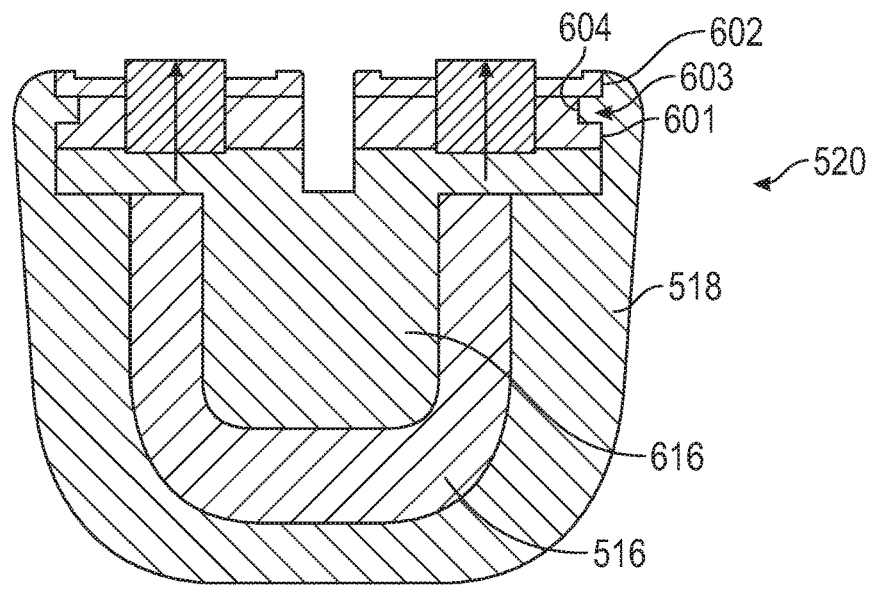
FIG. 6C is an enlarged, cross-sectional view of the jaw member of FIG. 6A illustrating a two-plate construction secured by an overmold layer vertically extending through openings formed in first and second base plates.

Referring to FIGS. 6A to 6C, the first base plate 601 may include an opening aligned with an opening formed in the second base plate 602. An overmold layer (e.g., the overmold layer 518 or an overmold layer 616) may extend through the openings formed in the first and second base plates 601 and 602 (see, e.g., vertical arrows illustrated in FIG. 6C). The extended overmold layer may form spacers (see, e.g., spacers 304 and 504) and/or may form the capture tabs 509 and/or may form mold-through dots 704.

Referring to FIGS. 3A to 3C and 6A to 6C, a method of manufacturing an electrosurgical instrument includes: positioning the first base plate 601 including a plurality of indents (see, e.g., indents 305) on a first jaw member 520 of an end effector assembly; positioning one or more spacers (e.g., spacer 304 or 504) in an indent of the plurality of indents; positioning the second base plate 602 on the first base plate 601 and on the one or more spacers, the second base plate 602 including one or more openings (see, e.g., opening 303) defined therein that exposes a surface of the spacer facing away from the first base plate 601, and the second base plate 602 forming a laterally facing attachment notch 603 with the first base plate; forming the overmold layer 518 about the first jaw member 520 in the laterally facing attachment notch 603 to secure the first and second base plates 601 and 602 to the first jaw member 520, which may be referred to herein as a lateral securing feature.

Referring particularly to FIG. 6C, according to an exemplary embodiment of the present disclosure, the method includes forming a first overmold layer 616 about the first jaw member 520 to penetrate each of first and second openings of the first and second base plates 601 and 602, the first overmold layer 616 vertically securing the first and second base plates 601 and 602 to the first jaw member 520, which may be referred to herein as a vertical securing feature, the first overmold layer 616 also forming spacers, capture tabs or mold-through dots, as described herein. The method also includes forming a second overmold layer 518 about, in part, the first overmold layer 616 in the laterally facing attachment notches 603, the second overmold layer 518 laterally securing the first and second base plates 601 and 602 to the first jaw member 520.

According to an exemplary embodiment of the present disclosure, a spacer (e.g., spacer 304 or 504) as described herein may be secured to the first jaw member 520 to secure the first and second base plates 601 and 602 to the first jaw member 520. This may be referred to herein as a spacer securing feature.

Thus, as described herein, a first vertical securing feature, a second lateral securing feature and/or a third spacer securing feature may be employed to secure the first and second base plates 601 and 602 to the first jaw member 520.

Figure 7A:
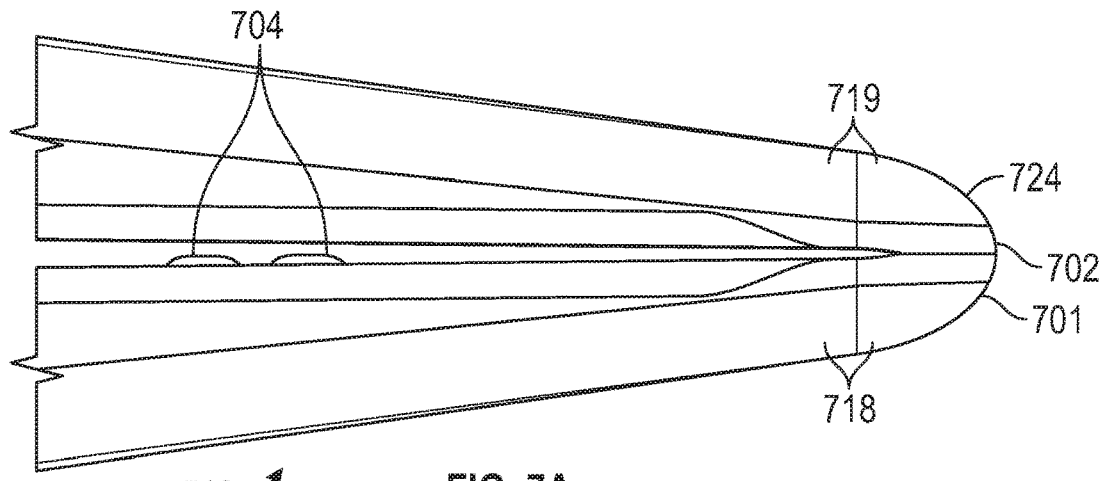
FIG. 7A is an enlarged, side view of an electrosurgical instrument including mold-through dots according to the present disclosure with jaw members of the end effector assembly disposed in a closed position having tip protrusions.
Figure 7B:
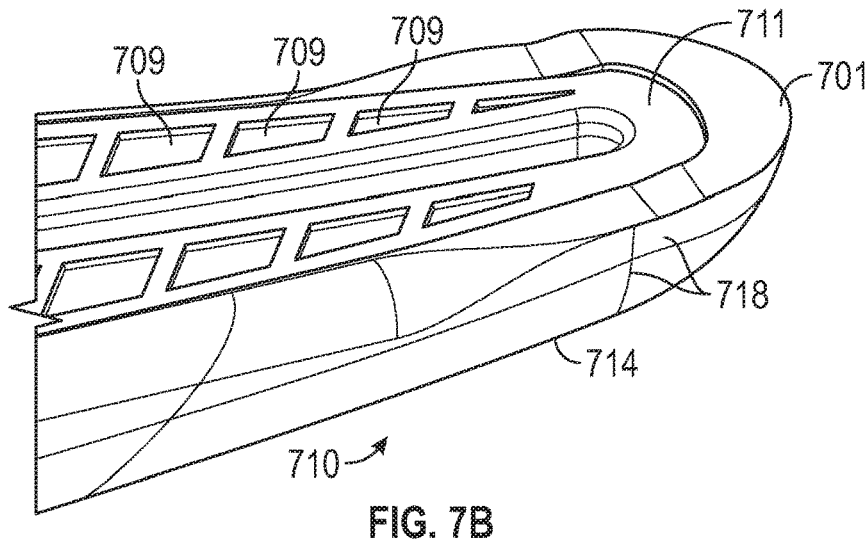
FIG. 7B is an enlarged perspective view of a jaw member of the end effector assembly of FIG. 7A having a tip protrusion.

Referring to FIGS. 7A and 7B, jaw members 710 and/or 720 include mold-through dots 704 disposed thereon. Jaw member 710 includes tip protrusion 701. Jaw member 720 includes tip protrusion 702. Tip protrusions 701 and 702 are positioned to contact each other when jaw members 710 and 720 are in a closed configuration. As pressure is applied to tip protrusions 701 and 702, jaw members 710 and 720 flex toward each other such that jaw members 710 and 720 contact the mold-through dots 704 on the opposing jaw member to maintain a desired distance between the jaw members 710 and 720. Alternatively, jaw members 710 and 720 may be substantially parallel to each other such that an opposing jaw member 710 or 720 contacts the mold-through dots 704 on the opposite jaw member without jaw members 710 and 720 flexing toward each other. The jaw members 710 and 720 each include a plurality of capture indents 709 forming a textured jaw surface. Each of the capture indents 709 is recessed below the respective surfaces of one of the first or second jaw member 710 or 720. The mold-through dots 704 may be formed by growing overmold layers (e.g., 616 or 518) through openings formed in base plates 601 and 602, similarly to how the capture tabs 509 may be formed (see, e.g., the vertical securing feature described above with reference to FIGS. 3A to 3C and 6A to 6C).

Referring to FIGS. 6A to 6C and 7A to 7B, a first overmold layer 718 is formed about the first jaw member 710. The first overmold layer 718 forms a first tip protrusion 701 at a distal portion 714 of a first jaw member 710. The spacer (e.g., spacer 304 or 504) and the first tip protrusion 701 maintain a substantially continuous distance between the first and second jaw members 710 and 720 in the closed position. The first tip protrusion 701 may also be formed using overmold layers 616 or 518.

A second overmold layer 719 is formed about the second jaw member 720. The second overmold layer 719 forms a second tip protrusion 702 at a distal portion 724 of the second jaw member 720. The second tip protrusion 702 directly contacts the first tip protrusion 701 when the first and second jaw members 710 and 720 are in the closed position.

The spacer, in combination with the first tip protrusion 701, maintains a substantially continuous distance between the first and second jaw members 710 and 720 in the closed position. However, it is also anticipated that the first tip protrusion 701 alone, or the second tip protrusion 702 alone, or the combination of the first and second tip protrusions in the absence of the spacer, could maintain the distance between the first and second jaw members 710 and 720 in the closed position, provided that a maximum threshold of force is not applied to the first and second jaw members 710 and 720 to force the first and second jaw members 710 and 720 together.

Referring again to FIGS. 3A to 4 and 7A to 7B, the first and second base plates (e.g., 301 and 302, or 601 and 602) may form an overhang 711 extending distally from the first jaw member 710. The first overmold layer 718 is formed about the overhang 711 formed by the first and second base plates. The first overmold layer 718 provides support for the overhang 711, such that the overhang 711 can maintain the distance between the first and second jaw members 710 and 720 in the closed position.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument, comprising:
   a housing;
   an elongated shaft extending from the housing;
   an end effector disposed at a distal portion of the elongated shaft and configured to deliver electrosurgical energy to tissue, the end effector including:
      a first jaw member having a first electrode plate and a second jaw member having a second electrode plate;
      a movable handle operably coupled to the housing and configured to move at least one of the first or second jaw members between an open position and a closed position;
      a first base plate disposed on the first jaw member;
      a second base plate disposed on the first base plate, the second base plate forming a series of laterally facing attachment notches with the first base plate such that the first and second base plates cooperate to bound each of the laterally facing attachment notches on at least four sides and each of the laterally facing attachment notches is unbounded along a laterally facing side of the first jaw member, the series of laterally facing attachment notches spaced apart from each other along the laterally facing side of the first jaw member; and
      an overmold layer formed about the first jaw member, the overmold layer disposed within the series of laterally facing attachment notches formed between the first and second base plates to secure the first and second base plates to the first jaw member.

2. The electrosurgical instrument of claim 1, wherein the second base plate includes an opening defined therein, and wherein a spacer is captured between the first base plate and the second base plate, the spacer protruding through the opening defined in the second base plate.

3. The electrosurgical instrument of claim 2, wherein the spacer is coupled to the first jaw member.

4. The electrosurgical instrument of claim 2, wherein the first base plate includes an opening aligned with the opening of the second base plate, and wherein the overmold layer extends through the openings of the first and second base plates.

5. The electrosurgical instrument of claim 2, wherein the spacer includes a lower portion having a first width and an upper portion have a second width smaller than the first width.

6. The electrosurgical instrument of claim 2, wherein the spacer includes metal, ceramic or glass.

7. The electrosurgical instrument of claim 1, wherein the end effector includes a knife configured to cut tissue disposed between the first and second jaw members.

8. The electrosurgical instrument of claim 1, further comprising an activation button extending from the housing and in registration with the movable handle, wherein selective actuation of the movable handle controls the delivery of electrosurgical energy to the first and second jaw members.

9. The electrosurgical instrument of claim 1, wherein the first base plate and the second base plate are mechanically welded together.

10. The electrosurgical instrument of claim 1, wherein the first and second base plates cooperate to bound each of the laterally facing attachment notches on five sides.

11. An end effector for an electrosurgical instrument, comprising:
    a first jaw member having a first electrode plate and a second jaw member having a second electrode plate;
    a first base plate disposed on the first jaw member;
    a second base plate disposed on the first base plate, the second base plate forming a series of laterally facing attachment notches with the first base plate such that the first and second base plates cooperate to bound each of the laterally facing attachment notches on at least four sides and each of the laterally facing attachment notches is unbounded along a laterally facing side of the first jaw member, the series of laterally facing attachment notches spaced apart from each other along the laterally facing side of the first jaw member; and an overmold layer formed about the first jaw member, the overmold layer disposed within the series of laterally facing attachment notches formed between the first and second base plates to secure the first and second base plates to the first jaw member.

12. The end effector of claim 11, wherein the second base plate includes an opening defined therein, and wherein a spacer is captured between the first base plate and the second base plate, the spacer protruding through the opening defined in the second base plate.

13. The end effector of claim 12, wherein the spacer is coupled to the first jaw member.

14. The end effector of claim 12, wherein the first base plate includes an opening aligned with the opening of the second base plate, and wherein the overmold layer extends through the openings of the first and second base plates.

15. The end effector of claim 12, wherein the spacer includes a lower portion having a first width and an upper portion have a second width smaller than the first width.

16. The end effector of claim 11, wherein the spacer includes metal, ceramic or glass.

17. The end effector of claim 11, further including a knife configured to cut tissue disposed between the first and second jaw members.

18. The end effector of claim 11, wherein the first and second jaw members are configured to receive electrosurgical energy.

19. The end effector of claim 11, wherein the first base plate and the second base plate are mechanically welded together.

20. The end effector of claim 11, wherein the first and second base plates cooperate to bound each of the laterally facing attachment notches on five sides.

* * * * *